United States Patent [19]
Inagaki et al.

[11] Patent Number: 4,822,891
[45] Date of Patent: Apr. 18, 1989

[54] 4-AMINO-2,3-DI-SUBSTITUTED-1-(MONO- OR TRICHLOROPHENYL)-3-PYRAZOLIN-5-ONES

[75] Inventors: Yoshio Inagaki; Tadao Shishido, both of Kanagawa, Japan

[73] Assignee: Fuji Photo Film Co., Ltd., Kanagawa, Japan

[21] Appl. No.: 13,593

[22] Filed: Feb. 11, 1987

Related U.S. Application Data

[63] Continuation of Ser. No. 858,830, Apr. 29, 1986, Pat. No. 4,711,963, which is a continuation-in-part of Ser. No. 459,028, Jan. 18, 1983, abandoned.

[30] Foreign Application Priority Data

Jan. 18, 1982 [JP] Japan ................... 57-6606

[51] Int. Cl.$^4$ .......................... C07D 231/46
[52] U.S. Cl. .................................. 548/365
[58] Field of Search ........................ 548/365

[56] References Cited

U.S. PATENT DOCUMENTS 4,247,631 1/1981 Nix et al. .................. 435/10

Primary Examiner—Robert W. Ramsuer
Attorney, Agent, or Firm—Sughrue, Mion, Zinn, Macpeak, and Seas

[57] ABSTRACT

Novel compounds are disclosed which are 4-amino-2,3-di-substituted-1-(mono- or trichlorophenyl)-3-pyrazolin-5-ones-representing by the following formulae (1) to (3);

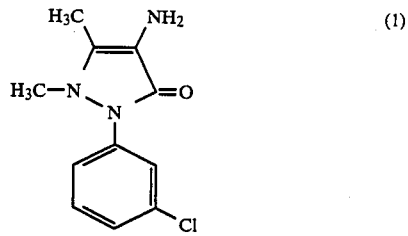

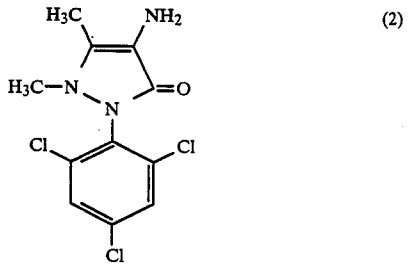

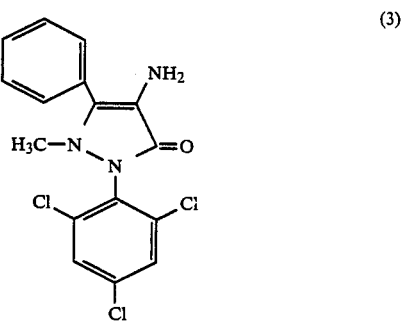

and acid addition salts thereof. The compounds can be easily produced and are useful for qualitative analysis or quantitative analysis of hydrogen peroxide when used as a component of a color indicator composition for detecting hydrogen peroxide.

10 Claims, 2 Drawing Sheets

4-AMINO-2,3-DI-SUBSTITUTED-1-(MONO- OR TRICHLOROPHENYL)-3-PYRAZOLIN-5-ONES

This is a continuation of application Ser. No. 06/858,830, filed Apr. 29, 1986 now U.S. Pat. No. 4,711,963, which is a continuation-in-part of application Ser. No. 06/459,028 filed Jan. 18, 1983, now abandoned.

FIELD OF THE INVENTION

The present invention relates to substituted derivatives of 4-amino-3-pyrazolin-5-one.

BACKGROUND OF THE INVENTION

Hydrogen peroxide is a reaction product produced by many enzymatic reactions in which oxidase takes part. For example, reactions such as oxidation of glycerine by glycerine oxidase, oxidation of glucose by glucose oxidase, or oxidation of cholesterol by cholesterol oxidase, are very important for analyses, particularly in the area of medical diagnostics.

Known methods for measuring hydrogen peroxide which is enzymatically formed are based on a titrimetric method, potentiometry, polarography, quantitative colorimetry, and an enzymatic method using the enzyme catalase or peroxidase. In accordance with a method for enzymatic measurement using peroxidase, a chromogen which reacts with hydrogen peroxide in the presence of peroxidase to form a dye which can be measured by photometry is used as an indicator. These kinds of known reagents for measuring hydrogen peroxide include an indicator system described in Trinder. Ann. Clin. Biochem., Vol. 6 (1969), pages 24–27. In this system, measurement is carried out using photometry after phenol is allowed to oxidatively bond with the chromogen:4-aminoantipyrine in the presence of peroxidase by the action of hydrogen peroxide. It is possible to use other phenol compounds such as 1,7-dihydroxynaphthalene instead of phenol.

When the compounds of the present invention are allowed to react with hydrogen peroxide in the presence of peroxidase and a known color former (for example, phenol, p-chlorophenol, 1,7-dihydroxynaphthalene, N,N-di-substituted m-toluidine, etc.), a dye is formed by an oxidative coupling reaction. Accordingly, if the resulting dye is quantitatively measured by colorimetry, the amount of hydrogen peroxide can be determined. Accordingly, if various oxidase type enzymes and their substrates which are already used for clinical examination are coexistent, instead of carrying out the direct action of hydrogen peroxide, the amount of hydrogen peroxide formed by an enzyme reaction can be determined. As a result, it is possible to determine the activity of these enzymes and the amount of the substrates (for example, glucose, uric acid, GPT (glutamyl-pyruvate transaminase), GOT (glutamyl-oxaloacetate transaminase), creatinine, etc.).

Conventionally, the quantitative analysis based on such a principle has been carried out by so-called wet quantitative analysis which is carried out in a solution in a test tube. Recently, so-called dry quantitative analysis using a multilayer analysis sheet having a reagent layer containing a reagent has been developed. The compounds of the present invention can be incorporated in the reagent layer of such a multilayer analysis sheet, by which good results are obtained.

SUMMARY OF THE INVENTION

An object of the present invention is to provide 4-amino-2,3-di-substituted-1-(mono- or trichlorophenyl)-3-pyrazolin-5-ones represented by the following chemical formulae (1) to (3) and acid addition salts thereof:

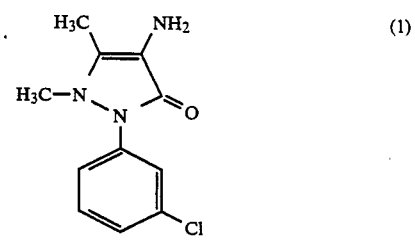

(1)

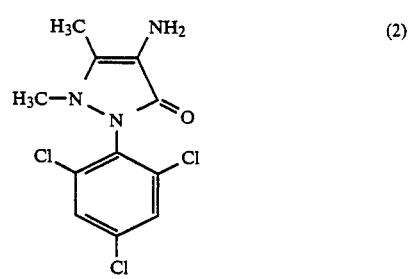

(2)

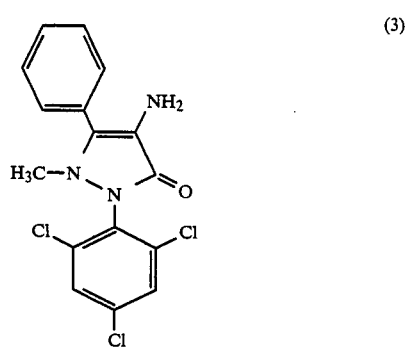

(3)

DETAILED DESCRIPTION OF THE INVENTION

Figure 1:
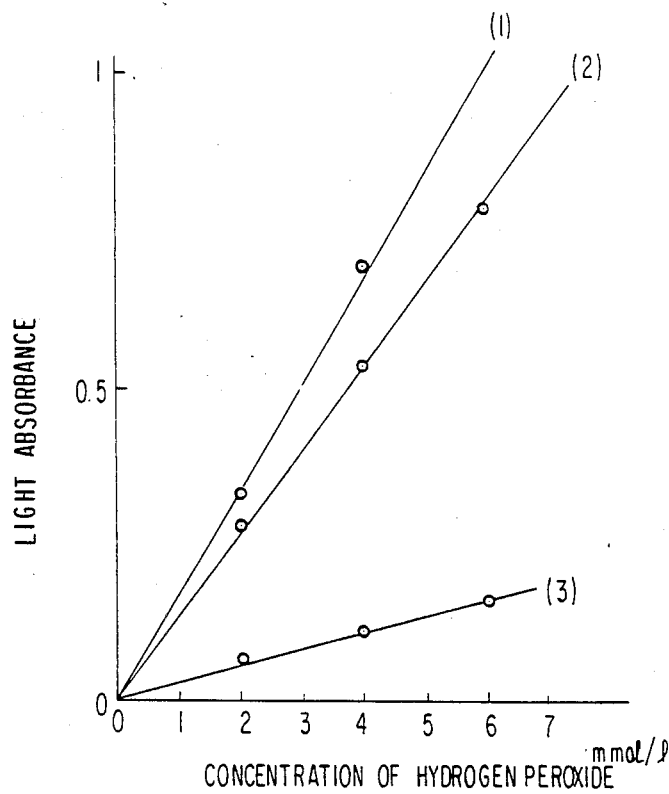
FIG. 1 is a graph which indicates the relation between the concentration (abscissa) and the light absorbance (ordinate) of the aqueous solution of hydrogen peroxide used in the process described in Example 4. The straight lines (1), (2), and (3) are obtained by plotting the measured values of solutions containing Compound (1) (hydrochloride), Compound (2), and Compound (3), respectively.

Three kinds of compounds of the present invention can be produced by the following reactions.

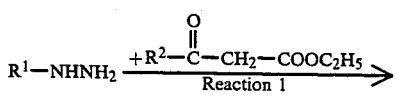

-continued

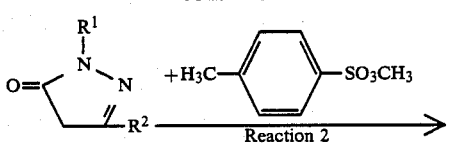

Reaction 2

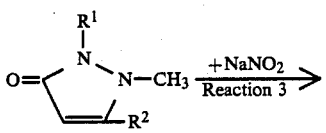

Reaction 3

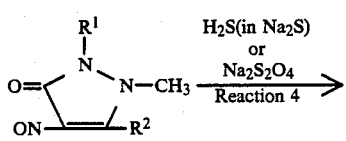

Reaction 4

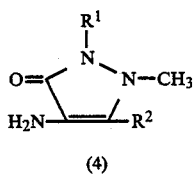

(4)

In Reactions 1 to 4, R¹ and R² represent the following combinations.

|  | Compound | | |
| --- | --- | --- | --- |
|  | (1) | (2) | (3) |
| R¹ | 3-Chlorophenyl group | 2,4,6-Trichlorophenyl group | 2,4,6-Trichlorophenyl group |
| R² | Methyl group | Methyl group | Phenyl group |

Acid addition salts of compounds represented by the formula (4), namely, 4-ammonio-2,3-di-substituted-1-(mono- or trichlorophenyl)-3-pyrazolin-5-ones can be produced by reacting the compound represented by the formula (4) with an acid according to the conventional method.

Three kinds of compounds of the present invention are as follows:

Compound (1): 4-Amino-2,3-dimethyl-1-(3-chlorophenyl)-3-pyrazolin-5-one

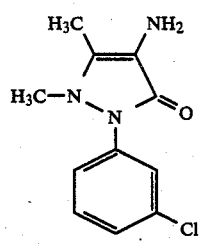

(1)

or acid addition salts thereof.

Compound (2): 4-Amino-2,3-dimethyl-1-(2,4,6-trichlorophenyl)-3-pyrazolin-5-one

(2)

or acid addition salts thereof.

Compound (3): 4-Amino-2-methyl-3-phenyl-1-(2,4,6-trichlorophenyl)-3-pyrazolin-5-one

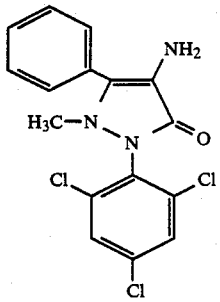

(3)

or acid addition salts thereof.

In each compound, examples of acids which form acid addition salts include inorganic acids such as hydrochloric acid, hydrobromic acid, hydroiodic acid, nitric acid, perchloric acid, sulfuric acid, etc. and organic acids such as acetic acid, oxalic acid, tartaric acid, p-toluenesulfonic acid, picric acid, picrolonic acid, etc. Examples of preferable acid addition salts are hydrochloric acid addition salts.

In the present specification, the compounds are named according to the regulation described in IUPAC nomenclature for organic chemistry, revised edition for synthetic recommendation in 1978.

The compounds of the present invention can be used for qualitative analysis or quantitative analysis of hydrogen peroxide, when they are used as a component of a color indicator composition for detecting hydrogen peroxide. Particularly, they can be suitably used as a component of color indicators for detecting hydrogen peroxide for clinical examination by combining with oxidase which is capable of forming hydrogen peroxide.

In the following, a process for synthesizing compounds of the present invention is illustrated in detail.

EXAMPLE 1

Synthesis of Hydrochloride of Compound (1)

(1) Reaction 2: Synthesis of 1-(3-Chlorophenyl)-2,3-dimethyl-3-pyrazolin-5-one 90 g of p-toluenesulfonic acid was added to 50 g of 1-(3-chlorophenyl)-3-methyl-2-pyrazolin-5-one [Chemical Abstracts Registry Number (90-31-3)], and the resulting mixture was stirred on an oil bath at 150° C. for 2.5 hours. The reaction mixture was allowed to cool down to 100° C. or less. A solution prepared from 25 g of sodium hydroxide and 150 ml of water was added dropwise thereto. After adding thereto 350 ml of water, the mixture was extracted with chloroform. The chloroform phase was separated and then dried over anhydrous potassium carbonate. After insoluble materials were filtered off, the filtrate was concentrated to dryness to obtain 28.1 g of 1-(3-chlorophenyl)-2,3-dimethyl-3-pyrazolin-5-one. When recrystallization was carried out from ethyl acetate, crystals having a melting point of 98° to 100° C. were obtained.

(2) Reaction 3: Synthesis of 1-(3-Chlorophenyl)-2,3-dimethyl-4-nitroso-3-pyrazolin-5-one To 11 g of 1-(3-chlorophenyl)-2,3-dimethyl-3-pyrazolin-5-one obtained by Reaction 2 were added 30 ml of water and 4.2 ml of conc. hydrochloric acid, and the resulting mixture was cooled with water. To the resulting solution was added dropwise a solution prepared by dissolving 3.4 g of sodium nitrite in 20 ml of water. A green precipitate thus formed was collected by filtration and then washed with water to obtain the titled compound. Yield: 10.5 g. Melting point: 163° C. (decomposition).

(3) Reaction 4: Synthesis of Hydrochloride of Compound (1)

To 5.5 g of 1-(3-chlorophenyl)-2,3-dimethyl-4-nitroso-3-pyrazolin-5-one obtained by Reaction 3 were added 0.1 g of sodium sulfide and 30 ml of water, and a hydrogen sulfide gas was introduced thereinto at 30° C. over 15 minutes such that the green color of the nitroso compound disappeared. After the reaction solution was extracted with ethyl acetate and dried over anhydrous sodium sulfate, insoluble matters were filtered off, and the ethyl acetate was removed by distillation. The residue was dissolved in 50 ml of tetrahydrofuran (THF), and a hydrogen chloride gas was introduced thereinto. The resulting precipitate was filtered off and washed with THF to obtain the titled compound. Yield: 2.8 g. Melting point: 185° C. (decomposition).

Figure 2:
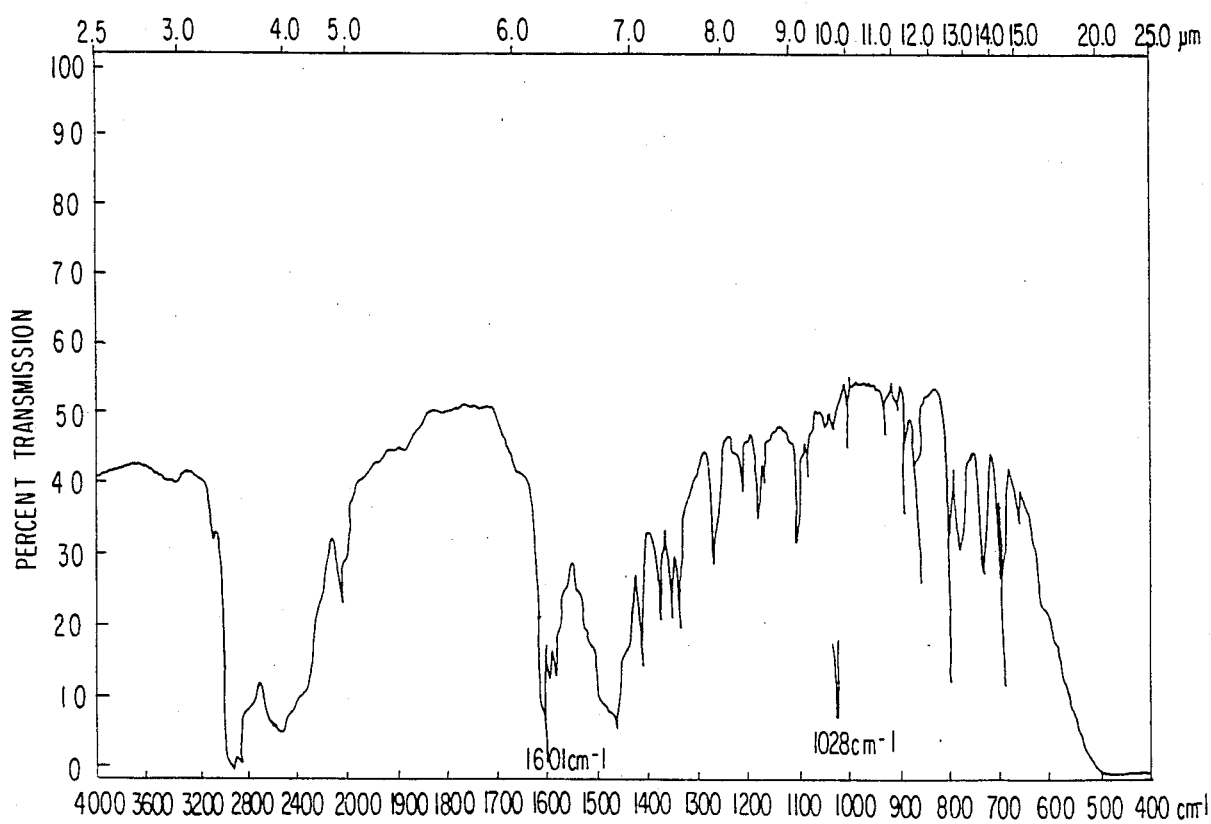
FIGS. 2 to 4 are infrared ray absorption spectra of Compound (1) (hydrochloride), Compound (2), and Compound (3) which are synthesized according to the process described in Examples 1 to 3, respectively.

The infrared ray absorption spectrum of the resulting hydrochloride of Compound (1) is shown in FIG. 2. A sample used for measuring the infrared ray absorption spectrum was that prepared by grinding hydrochloride of Compound (1) together with liquid paraffin and putting the resulting mixture between rock salt plates.

EXAMPLE 2

Synthesis of Compound (2)

(1) Reaction 1: Synthesis of 3-Methyl-1-(2,4,6-trichlorophenyl)-2-pyrazolin-5-one To 280 g of 2,4,6-trichlorophenylhydrazine was added 180 ml of ethyl acetoacetate, and the resulting mixture was stirred at room temperature for 30 minutes. After adding thereto a solution prepared by dissolving 215 g of potassium hydroxide in 7 l of ethanol, the reaction solution was refluxed with heating for 1 hour. The reaction solution was poured into 6 l of water and neutralized with conc. hydrochloric acid. After being cooled to room temperature, a precipitate thus formed was filtered off, washed with water, and then dried under reduced pressure to obtain the titled compound. Yield: 300 g. Melting point: 178° to 180° C.

(2) Reaction 2: Synthesis of 2,3-Dimethyl-1-(2,4,6-trichlorophenyl)-2-pyrazolin-5-one To 140 g of 3-methyl-1-(2,4,6-trichlorophenyl)-2-pyrazolin-5-one obtained by Reaction 1 was added 188 g of methyl p-toluenesulfonate, and the resulting mixture was stirred with heating on an oil bath at 160° C. for 2 hours. After being allowed to cool to 100° C. or less, a solution prepared by dissolving 60 g of sodium hydroxide in 1 liter of water was added dropwise thereto. After being neutralized with conc. hydrochloric acid, 500 ml of water was added thereto, and the mixture was extracted twice with 500 ml of chloroform. After being dried over anhydrous potassium carbonate, insoluble matters were removed off by filtration, and the residue was concentrated to dryness. A solid thus formed was recrystallized from ethyl acetate to obtain the titled compound. Yield: 87 g. Melting point: 151° to 153° C.

(3) Reaction 3: Synthesis of 2,3-Dimethyl-4-nitroso-1-(2,4,6-trichlorophenyl)-3-pyrazolin-5-one To 80 g of 2,3-dimethyl-1-(2,4,6-trichlorophenyl)-3-pyrazolin-5-one obtained by Reaction 2 were added 400 ml of acetic acid and 200 ml of water for dissolution. After adding thereto 30 ml of conc. hydrochloric acid, the solution was cooled to 5° C. A solution prepared by dissolving 24.5 g of sodium nitrite in 150 ml of cold water was further added thereto. The precipitated bluish green crystals were filtered off, washed with water, and then dried to obtain the titled compound. Yield: 71.7 g. Melting point: 214° C. (decomposition).

(4) Reaction 4: Synthesis of Compound (2)

To 70 g of 2,3-dimethyl-4-nitroso-1-(2,4,6-trichlorophenyl)-3-pyrazolin-5-one obtained by Reaction 3 were added 480 ml of ethanol and 80 ml of water. The resulting mixture was cooled to 10° C., and a solution prepared by dissolving 120 g of sodium hydrosulfide in 480 ml of cold water was added thereto. The mixture was stirred for 1 hour at 25° C. or less. The reaction solution was extracted twice with 280 ml of chloroform. The extract solution was dried over anhydrous sodium sulfate and concentrated to dryness. The resulting solid was dissolved in chloroform and washed with water. Then, it was concentrated again to dryness. The resulting solid was recrystallized from 120 ml of isopropyl alcohol to obtain the titled compound. Yield: 23.1 g. Melting point: 146° to 148° C.

Figure 3:
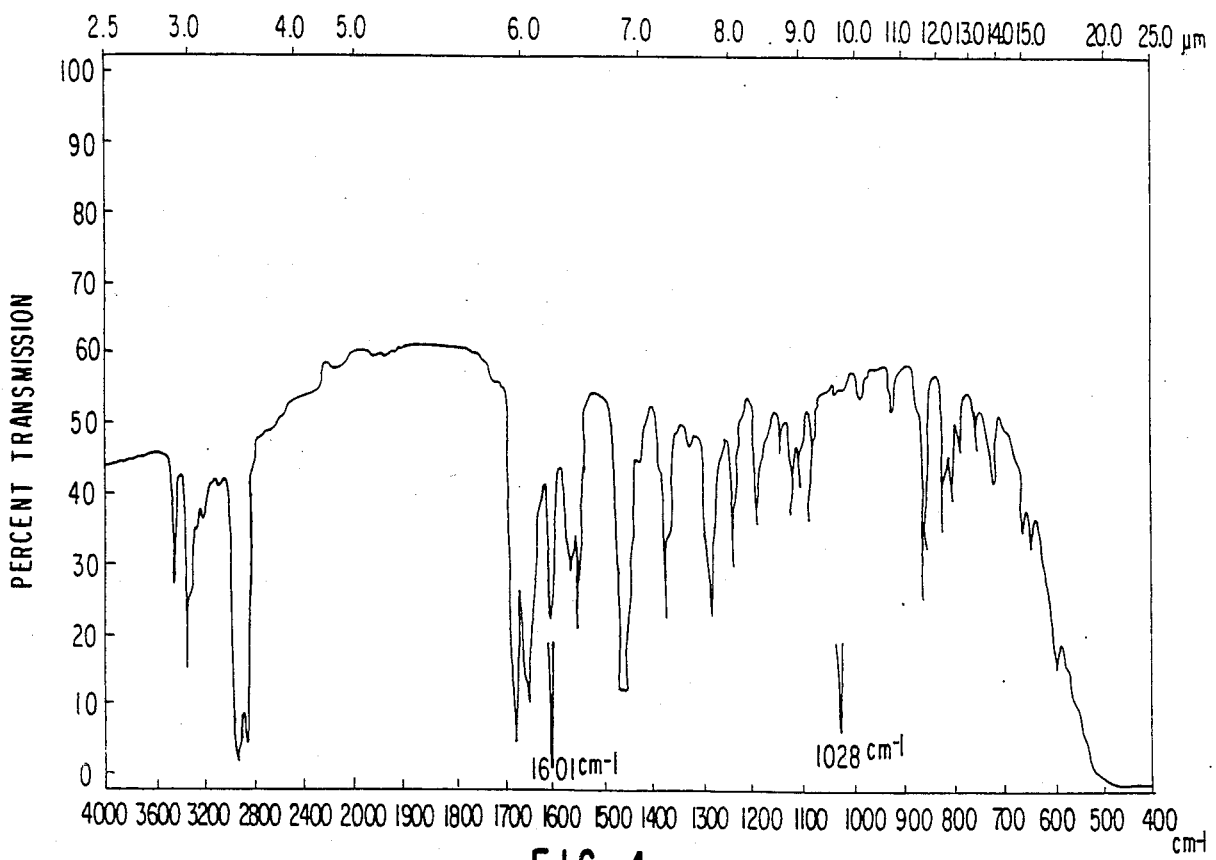

The infrared ray absorption spectrum of the Compound (2) measured by the same manner as in Example 1 is shown in FIG. 3.

EXAMPLE 3

Synthesis of Compound (3)

Compound (3) was obtained as a crystal having a melting point of 150° to 152° C. by carrying out the same procedure as in Example 2 except using ethyl benzoylacetate instead of the ethyl acetoacetate.

Figure 4:
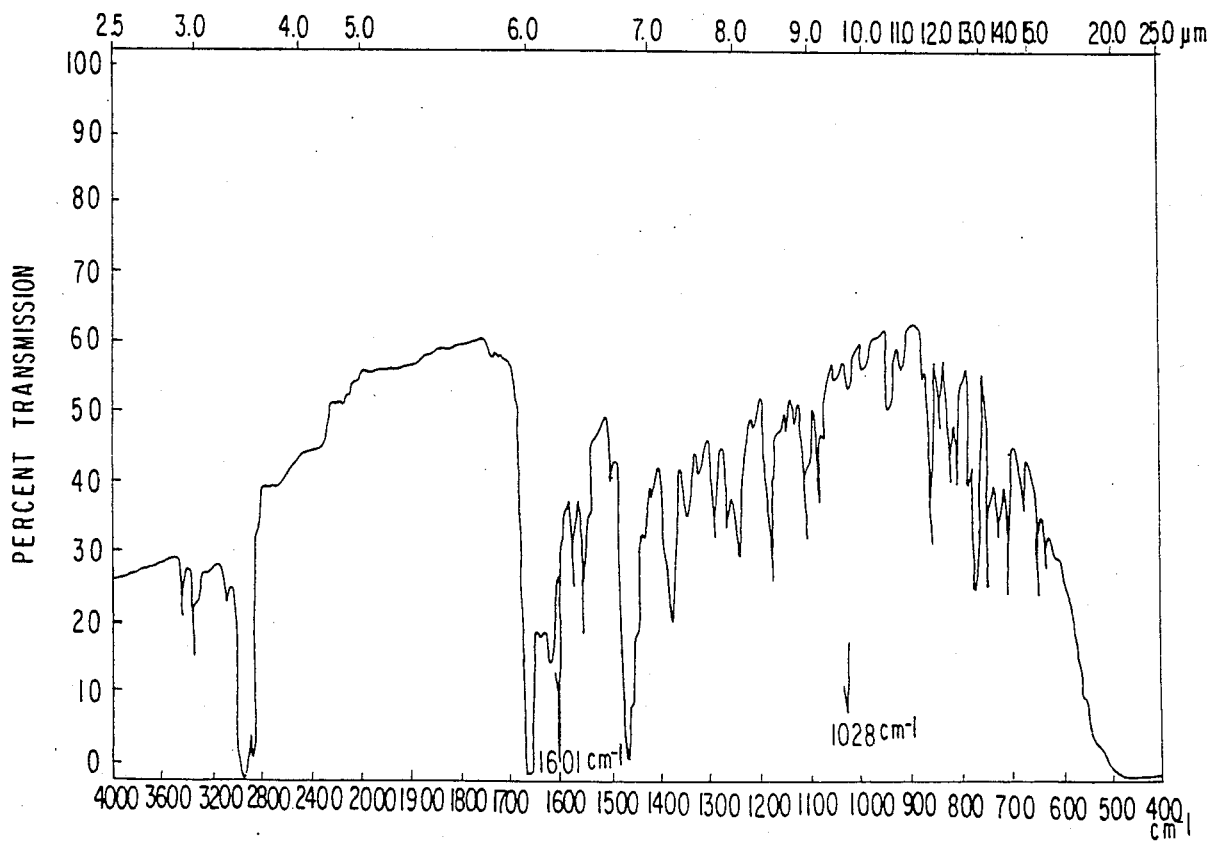

The infrared ray absorption spectrum of the Compound (3) measured by the same manner as in Example 1 is shown in FIG. 4.

The results of elemental analysis for the compounds of the present invention are shown in Table 1.

TABLE 1

| | Results of Elemental Analysis | | |
| | Percentage by Weight of Elements | | |
| Compound | C (%) | H (%) | N (%) |
| --- | --- | --- | --- |
| (1) Found | 42.51 | 4.35 | 13.39 |

TABLE 1-continued

| | | Results of Elemental Analysis | | |
|---|---|---|---|---|
| | | Percentage by Weight of Elements | | |
| Compound | | C (%) | H (%) | N (%) |
| | Calculated | 42.67 | 4.23 | 13.57 |
| (2) | Found | 43.25 | 3.23 | 13.61 |
| | Calculated | 43.10 | 3.29 | 13.71 |
| (3) | Found | 52.01 | 3.21 | 11.35 |
| | Calculated | 52.13 | 3.28 | 11.40 |

EXAMPLE 4

Use Example

To 50 units of peroxidase and 10 μmols of Compound (1) (hydrochloride) was added 25 ml of a 1/15 mol phosphoric acid buffer solution and then 0.5 ml of an acetone solution containing 50 μmols of N,N-bis-β-dihydroxy-m-toluidine. Thereafter, a 1/15 mol phosphoric acid buffer solution was further added thereto to prepare 50 ml of an aqueous solution. Likewise, aqueous solutions containing Compound (2) and Compound (3), respectively, were prepared.

5 ml portions were sampled from these three kinds of solutions, and they were put in three test tubes, respectively (a total of 9 test tubes). All test tubes were heated to 37° C. for 3 minutes. Then, 50 μl of an aqueous solution of hydrogen peroxide having a known concentration (three of 2.0 μmol/l, 4.0 μmol/l, and 6.0 μmol/l) was added to each test tube. After being heated to 37° C. for 10 minutes, the light absorbance of each solution at absorption maximum wavelength was measured. The absorption maximum wavelength was 555 nm, 545 nm, and 555 nm in each of the solutions containing Compounds (1), (2) and (3), respectively.

It has been understood that Compounds (1), (2) and (3) of the present invention can be effectively used for quantitative analysis of hydrogen peroxide, because measured values of light absorbance to concentration of hydrogen peroxide vary linearly according to the amount of hydrogen peroxide as shown in FIG. 1. The light absorbance is based on a value of blank measured as a control.

While the invention has been described in detail and with reference to specific embodiment thereof, it will be apparent to one skilled in the art that various changes and modifications can be made therein without departing from the spirit and scope thereof.

What is claimed is:

1. 4-amino-2,3-di-substituted-1-(mono- or trichlorophenyl)-3-pyrazolin-5-ones represented by the following formulae (1) and (2):

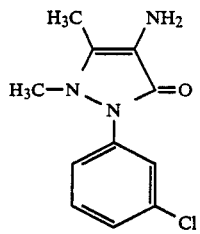

(1)

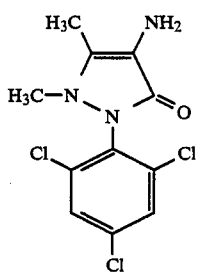

(2)

2. A compound as claimed in claim 1, which is 4-amino-2,3-dimethyl-1-(3-chlorophenyl)-3-pyrazolin-5-one.

3. A compound as claimed in claim 1, which is 4-amino-2,3-dimethyl-1-(2,4,6-trichlorophenyl)-3-pyrazolin-5-one.

4. An acid addition salt of a 4-amino-2,3-di-substituted-1-(mono- or trichlorophenyl)-3-pyrazolin-5-one as claimed in claim 1.

5. An acid addition salt of a 4-amino-2,3-dimethyl-1-(3-chlorophenyl)-3-pyrazolin-5-one compound as claimed in claim 1.

6. An acid addition salt of a 4-amino-2,3-dimethyl-1-(2,4,6-trichlorophenyl)-3-pyrazolin-5-one compound as claimed in claim 1.

7. An acid addition salt of a 4-amino-2,3-di-substituted-1-(mono- or trichlorophenyl)-3-pyrazolin-5-one compound as claimed in claim 1, wherein the acid which forms said acid addition salt is an inorganic acid.

8. An acid addition salt of a 4-amino-2,3-di-substituted-1-(mono- or trichlorophenyl)-3-pyrazolin-5-one compound as claimed in claim 7, wherein said inorganic acid is selected from the group consisting of hydrochloric acid, hydrobromic acid, hydroiodic acid, nitric acid, perchloric acid, and sulfuric acid.

9. A acid addition salt of a 4-amino-2,3-di-substituted-1-(mono- or trichlorophenyl)-3-pyrazolin-5-one compound as claimed in claim 1, wherein the acid which forms said acid addition salt is an organic acid.

10. An acid addition salt of a 4-amino-2,3-di-substituted-1-(mono- or trichlorophenyl)-3-pyrazolin-5-one compound as claimed in claim 9, wherein said organic acid is selected from the group consisting of acetic acid, oxalic acid, tartaric acid, p-toluenesulfonic acid, picric acid, and picrolonic acid.

* * * * *